(12) United States Patent
Barber, III et al.

(10) Patent No.: US 8,247,586 B2
(45) Date of Patent: Aug. 21, 2012

(54) METHODS OF MAKING LAYERED MIXED-METAL PHOSPHONATES FOR HIGH DIELECTRIC STRENGTH POLYMER NANOCOMPOSITES

(75) Inventors: Arthur Peter Barber, III, West Columbia, SC (US); Harry J. Ploehn, Columbia, SC (US); Hans-Conrad zur Loye, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 13/329,731

(22) Filed: Dec. 19, 2011

(65) Prior Publication Data

US 2012/0095142 A1 Apr. 19, 2012

Related U.S. Application Data

(62) Division of application No. 12/705,761, filed on Feb. 15, 2010, now Pat. No. 8,080,600.

(60) Provisional application No. 61/207,631, filed on Feb. 13, 2009.

(51) Int. Cl.
*C07F 9/02* (2006.01)

(52) U.S. Cl. .......... 556/19; 534/15; 556/174; 562/8
(58) Field of Classification Search .......... 556/19, 556/174; 534/15; 562/8
See application file for complete search history.

(56) References Cited

OTHER PUBLICATIONS

Cao et al. "Formation of quantum-size semiconductor particles in a layered metal phosphonate host lattice", Chem. Mater. 1991, 3, 149-156.*

* cited by examiner

*Primary Examiner* — Vickey Nerangis
*Assistant Examiner* — Wenwen Cai
(74) *Attorney, Agent, or Firm* — Dority & Manning, P.A.

(57) ABSTRACT

Multi-metal phosphonates are generally provided. The multi-metal phosphonate can generally have the composition: $AB(RPO_3)_3$, where A is $Mg^{2+}$, $Ca^{2+}$, $Sr^{2+}$, $Ba^{2+}$, $Pb^{2+}$, $La^{3+}$, or combinations thereof; B is $Ti^{4+}$, $Zr^{4+}$, $Al^{3-}$, or combinations thereof; and R is an organic group (e.g., aryl group, an alkyl group, an alkenyl group, etc.). The multi-metal phosphonate can be combined with a polymeric material to form a polymeric film. Methods of making the multi-metal phosphonate by combining and reacting a metal oxide and an organophosphonic acid are also provided.

19 Claims, 16 Drawing Sheets

| EDS | Atomic % Sr | Atomic % Ti |
|---|---|---|
| Position 1 | 48.80 | 51.20 |
| Position 3 | 50.74 | 49.26 |
| Position 4 | 50.49 | 49.51 |
| Position 5 | 48.81 | 51.19 |
| Position 6 | 49.22 | 50.78 |
| Average atomic ratio | 49.61 ± 1 | 50.38 ± 1 |
| XPS | Atomic % Sr (Ba) | Atomic % Ti |
| SrTi(PPA) | 48.56 ± 2 | 51.44 ± 2 |
| BaTi(PPA) | 47.64 ± 2 | 52.36 ± 2 |

Figure 16

METHODS OF MAKING LAYERED MIXED-METAL PHOSPHONATES FOR HIGH DIELECTRIC STRENGTH POLYMER NANOCOMPOSITES

PRIORITY INFORMATION

The present application claims priority to U.S. patent application Ser. No. 12/705,761 filed on Feb. 15, 2010, titled "Layered Mixed-Metal Phosphonates for High Dielectric Strength Polymer Nanocomposites" of zur Loye, et al., and provisional patent application Ser. No. 61/207,631 filed on Feb. 13, 2009 titled "Layered Mixed-Metal Phosphonates for High Dielectric Strength Polymer Nanocomposites" of zur Loye, et al., the disclosures of which are incorporated by reference herein.

GOVERNMENT SUPPORT CLAUSE

The present invention was developed with government support and funding from the United States Air Force, UTC under award 22040-FA21. The government has certain rights in this invention.

BACKGROUND

Commercially available, off-the-shelf capacitors simply cannot meet the extreme requirements of current and future industrial or military applications for intense, transient sources of high voltage pulse power. Furthermore, minimizing the component volume and weight are critical to the viability of new power storage systems for use in aircraft, spacecraft, and other mobile devices.

Existing dielectric capacitors have quite low energy densities, both on volume and mass basis. Electrochemical capacitors, including double layer capacitors and supercapacitors, offer high energy and power density, but their rate capability is limited by mass transfer and faradaic reaction rates. No current capacitor technology has the combination of energy density, power density, and rate capability required for new systems currently under development or envisioned for the future.

The maximum volumetric energy density W (J/cm³) stored by a dielectric capacitor, $$W = 0.5 \epsilon_0 \epsilon_r E_{bd}^2 \quad (1)$$

depends on the relative dielectric permittivity (or dielectric constant, $\epsilon_r$) and dielectric breakdown field strength ($E_{bd}$ in V/μm). For a parallel plate capacitor with area A, thickness d, and capacitance $C = \epsilon_0 \epsilon_r A/d$, we have the alternate expression $$W' \equiv AdW = 0.5 Cd^2 E_{bd}^2 = 0.5 CV_{bd}^2 \quad (2)$$

for the maximum energy W(J) stored by a capacitor charged to the breakdown voltage $V_{bd}$. The most obvious way to increase W' (or W) would be to choose dielectric materials with the highest possible breakdown field strength. Many polymers not only have high values of $E_{bd}$, but the also offer the additional advantage of processability. Unfortunately, the dielectric constants of most polymers are negligible.

The energy density could also be increased by blending high-$\epsilon_r$ inorganic ceramic materials into polymers, leading to higher effective dielectric constant. Many groups have attempted to disperse commercially available, high-$\epsilon_r$ ceramic oxides, such as barium titanate ($BaTiO_3$) into polymers followed by fabrication of thin films. Unfortunately, both experiment and theory show that the inorganic loading must be quite high to significantly increase the effective dielectric constant. For example, the symmetric Bruggeman equation, one of several effective medium theories, suggests that increases in $\epsilon_{eff}$ will not be observed until filler loadings are greater than 30% by volume. Conversely, there have also been many studies that show the Bruggeman equation grossly overestimates $\epsilon_{eff}$ and that achieving high $\epsilon_{eff}$ values requires inorganic ceramic particle loadings greater than 50% by volume.

A major problem that develops from high inorganic loadings in polymers (particularly $BaTiO_3$) is poor dispersion in the polymer matrix. The poor dispersion of inorganic in polymer leads to poor $\epsilon_{eff}$ and poor $\epsilon_{bd}$ caused by the domination of the $\epsilon_{bd}$ of the defect-rich inorganic filler network. The recent work by Kim et al. has shown that surface modification of $BaTiO_3$ by various organo-phosphonic acids leads to better dispersion of $BaTiO_3$ particles in the polymer matrix, to a high effective dielectric constant, and to only about a 50% decrease in breakdown field strength compared to polymer alone.

The recognition that polymer-filler interfaces can dominate capacitor performance leads naturally to the concept of polymer nanocomposite dielectrics. As such, a need exists for improved dispersion of inorganic loadings in a polymer matrix.

SUMMARY

Objects and advantages of the invention will be set forth in part in the following description, or may be obvious from the description, or may be learned through practice of the invention.

In general, the present disclosure is directed toward mixed metal phosphonates and their methods of manufacture. The mixed metal phosphonate can generally have the composition: $AB(RPO_3)_3$, where A is $Mg^{2+}$, $Ca^{2+}$, $Sr^{2+}$, $Ba^{2+}$, $Pb^{2+}$, $La^{3+}$, or combinations thereof; B is $Ti^{4+}$, $Zr^{4-}$, $Al^{3+}$, or combinations thereof; and R is an organic group (e.g., aryl group, an alkyl group, an alkenyl group, etc.). The mixed metal phosphonate can be combined with a polymeric material to form a polymeric film.

According to one embodiment, the mixed metal phosphonate can be made by combining a metal oxide and an organophosphonic acid in a sealed container then heating the metal oxide and the organophosphonic acid to a reaction temperature that is above the melting temperature of the organophosphonic acid and below the decomposition temperature of the organophosphonic acid. In an alternative embodiment, the mixed metal phosphonate can be made by combining a metal oxide and an organophosphonic acid in a solvent and boiling the solvent containing the metal oxide and the organophosphonic acid. In either method, the metal oxide can include $ABO_3$ where A is $Mg^{2+}$, $Ca^{2+}$, $Sr^{2+}$, $Ba^{2+}$, $Pb^{2+}$, $La^{3+}$, or combinations thereof; and B is $Ti^{4+}$, $Zr^{4+}$, $Al^{3+}$, or combinations thereof. The organophosphonic acid can include $RPO_3H_2$, where R is the organic group.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which:

FIG. 16 shows the EDS results for SrTi(PPA)$_3$ platelets imaged by HRTEM (FIG. 3), and XPS results for BaTi(PPA)$_3$ and SrTi(PPA)$_3$ bulk powders, according to the Examples.

DETAILED DESCRIPTION

Figure 1:
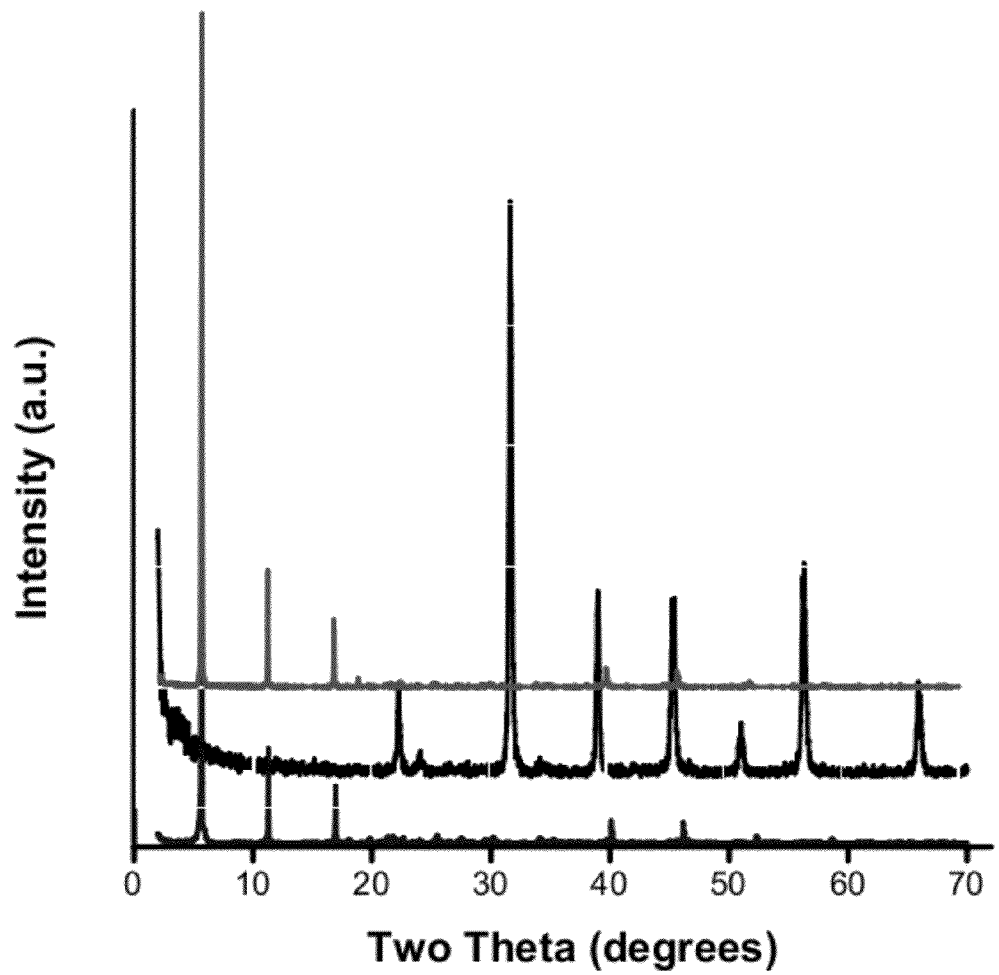
FIG. 1 shows powder XRD patterns of BaTiO$_3$ (middle pattern), BaTi(PPA)$_3$ (bottom pattern), and Ba(PPA) (top pattern) according to the Examples.

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Generally speaking, the present disclosure is directed to mixed metal phosphonates and their methods of making The mixed metal phosphonates can be synthesized from a metal oxide(s) in combination with organophosphonic acids. As such, the mixed metal phosphonates include the organic phosphonate within their chemical structure, as opposed to organically coated metal oxide particles. Thus, the mixed metal phosphonates contain an organic phosphonate group within the compound structure (e.g., covalently bonded), and can provide compatibility to the mixed metal phosphonates with other organic materials (e.g., polymeric material). For example, the organic group can be selected to provide compatibility (e.g., solubility, dispersability, etc.) with particular polymeric material and/or solvents. Additionally, the mixed metal phosphonates can still exhibit dielectric behavior similar to, but not tied to, their starting metal oxide. Thus, the mixed metal phosphonates are a new class of dielectric materials and, therefore, can be used to form polymeric dielectric films.

The metal oxide(s) used to synthesize the mixed metal phosphonate can generally be represented as ABO$_3$, where A is Mg$^{2-}$, Ca$^{2+}$, Sr$^{2+}$, Ba$^{2+}$, Pb$^{2+}$, La$^{3+}$, or combinations thereof and B is Ti$^{4+}$, Zr$^{4+}$, Al$^{3+}$, or combinations thereof. In one particular embodiment, the A and B cations can be paired such that A includes a cation having a valence of +2 and B includes a cation having a valence of +4. Alternatively, the A and B cations can be paired such that A includes a cation having a valence of +3 and B includes a cation having a valence of +3. Examples of suitable metal oxides include, but are not limited to, BaTiO$_3$, SrTiO$_3$, LaAlO$_3$, BaZrO$_3$, PbTiO$_3$, and mixtures thereof.

The metal oxide can be reacted with an organophosphonic acid, generally represented as RPO$_3$H$_2$, where R is the organic group. The organic group can be any suitable organic substituent. For example, suitable organic group include, but are not limited to, alkyl groups (e.g., methyl, ethyl, propyl, butyl, etc.), alkenyl groups (ethylene, propylene, butylene, etc.), aryl groups (e.g., phenyl, benzyl, etc.), and combinations thereof. Additionally, organophosphonic acids containing heteroatoms, such as sulfur, chlorine, bromine, nitrogen, etc. in the organic group can be used.

Generally, the mixed metal phosphonate formulated from the metal oxide(s) and the organophosphonic acid(s) can be represented as AB(RPO$_3$)$_3$, where A, B, and R are as discussed above.

In one particular embodiment, the organic group can be a phenyl group (where the organophosphonic acid is phenylphosphonic acid, known as "PPA") to form a mixed metal phosphonate of the formula AB(PPA)$_3$, which can readily disperse into toluene allowing easy fabrication of polystyrene-mixed-metal phosphonate nanocomposites.

The mixed metal phosphonates can be formed according to any suitable method. Suitable methods can include solution reaction methods, melt reaction methods, etc. The method of formulation can be selected according to the particular metal oxide(s) and organophosphonic acid(s) to be reacted.

For instance, the solution reaction method can be used to form the mixed metal phosphonates without limitations on the type of organic group in the organophosphonic acid, as long as both the metal oxide(s) and the organophosphonic acid(s) can be combined into a common solvent. However, since there are numerous available solvents, one skilled in the art should be able to find a common solvent for nearly every R groups on the organophosphonic acid(s). According to this method, the metal oxide(s) and the organophosphonic acid(s) are combined into a solvent(s) and heated under solvothermal conditions (e.g., heated above the boiling point of the solvent or solvent combination). As the mixed metal phosphonates begin to form, the mixed metal phosphonates will precipitate out of the reaction solution, and can be collected. The solvent can, in one embodiment, be selected to deprotonate the two hydroxyls of the phosphonic acid to facilitate the formation of the mixed metal phosphonates. Suitable solvents can include, but are not limited to, alcohols (e.g., methanol, ethanol, propanol, butanol, etc.), toluene, dimethyl sulfoxide (DMSO), hexane, benzene, chloroform, diethyl ether, tetrahydrofuran, ethyl acetate, acetone, dimethylformamide, acetic acid, formic acid, water, etc., and mixtures and combinations thereof.

In one embodiment, a stoichiometric excess of the organophosphonic acid can be included in the solution when compared to the stoichiometric amount of metal oxide present. Thus, the reaction can be conducted until all of the metal oxide is reacted into a mixed metal phosphonate. Then, the excess organophosphonic acid can be washed from the precipitated product.

The melt method is generally a condensation reaction that involves combining the metal oxide(s) and the organophosphonic acid(s) in a tube, sealing the tube to prevent the escape of gas (particularly water vapor, as water is a by-product of the condensation reaction, but is believed to be necessary for coordination to the metals and thus allowing the bridging phosphorus to be present) and heating the organophosphonic acid(s) above its melting point. Upon melting the organophosphonic acid(s) can react with the metal oxide(s) to form the mixed metal phosphonates. In particular, using a stoichiometric mixture (or a slight stoichiometric excess of organophosphonic acid, the acid melts containing the oxide, and as the product forms it becomes a solid. When the reaction is finished, only the mixed metal phosphonate product is left, with the slight excess of acid (if used) that can be washed out. Thus, similar to the solution method, the mixed metal phosphonate will precipitate out of the solution as it is formed. This reaction can be allowed to continue as desired, for example about 1 hour to about 1 week. In most situations, the reaction time can be 12 hours to 60 hours, such as 24 hours to 48 hours.

The melt method can provide more uniform reaction properties across different metal oxides. However, the melt method is limited to those organophosphonic acid(s) having a melting point lower then its decomposition point. Thus, not all R groups on the organophosphonic acid(s) can be utilized in the melt method.

The products formed according to both of these methods are crystalline.

No matter the method of formulation, the mixed metal phosphonate can be combined with an organic polymeric material. For instance, the polymeric material can be solubilized in a solvent. The mixed metal phosphonate can be dispersed into the solubilized polymeric material to form a substantially homogeneous mixture. The mixture can then be formed into a film by any method (e.g., spun coated, film cast, and the like).

The polymeric material can be selected to be compatible with the particular R group in the mixed metal phosphonate, so that the polymeric material and the mixed metal phosphonate can be more readily combined. For example, when the R group is a phenyl group, polystyrene can be used as the polymeric material and toluene can be used as the solvent.

EXAMPLES

Mixed-metal phenyl phosphonates have been successfully synthesized starting from the dielectric oxides $BaTiO_3$ and $SrTiO_3$. According to powder XRD patterns, the compounds are isostructural to their respective divalent metal phosphonate. From the HRTEM images of isolated stacks of platelets coupled with EDS, the distribution of the metals (Sr:Ti) was seen to be 1:1. From $^{31}P$-NMR experiments conducted on the mixed metal phosphonate system, that if the two metals separate from $[BaTi]^{6+}$ to $Ba^{2+}$ and $Ti^{4+}$, the Ti-phenyl phosphonate is the major product at 90%. The EDS results confirm that the metals stay together. Thermal analysis of the compounds further confirms the formation of the mixed metal system, since from powder XRD analysis of the thermal degradation products revealed a mixed metal gyro-phosphate, $ATi(P_2O_7)_{1.5}$, A=Ba, Sr.

Most importantly, these compounds still exhibit the same dielectric behavior as their starting oxide. The phenyl groups protruding in the inter-layer, allow for better dispersion of the compound into toluene. The dielectric permittivity of the PS composites increases with the better dispersion of the dielectric material. This is clearly seen in the direct comparison of the unmodified $BaTiO_3$ versus BaTi(PPA). The next step in the dielectric characterization of these mixed-metal phosphonates is to measure their effect on the breakdown voltage. Preliminary results on the breakdown voltage show no decrease in the value.

Experimental

Materials

Chemicals were obtained as reagent grade from commercial sources and used without any further purification.

Structure Characterization

FT-IR spectra were recorded on a Perkin Elmer Spectrum 100 using ATR diamond cell method. Powder X-ray diffraction patterns were collected using a Rigaku DMAX 2200 diffractometer. Thermogravimetric analysis was performed using a Thermal Analysis (TA) SDT-Q600 simultaneous DTA/TGA system in an oxidative environment. The samples were heated to 800° C. at a heating rate of 10° C./min. Solid-state 31P spectra were collected on a Varian Inova 500 spectrometer operating at 202.489 MHz using a Doty Scientific 4 mm/XC magic angle spinning(MAS) probe. Bloch decays of 50 msec were collected with a 200 ppm window after 45 degree excitation pulses. A relaxation delay of 10 secs was used between each transient. TPPM dipolar decoupling with a field strength of 45 kHz was applied during acquisition. A MAS speed of 10 kHz was used, and between 16 to 64 scans were collected for each run. Spectral deconvolution was performed with the standard routine included with Varian's VNMR 6.1C software. Platelet imaging and elemental analysis was collected using a JEOL 2100F 200 kV field-emission gun TEM/STEM with an Oxford Instruments INCA EDS solid-state X-ray detector. The capacitance measurements at 100 kHz and 1 MHz were made using a Keithley 590 CV Analyzer instrument. Impedance measurements from 10 Hz to 100 kHz were made using a 273A Model Potentiostat and EG&G 1025 Model Frequency Response Detector.

Hydrothermal Synthesis of $AB(RPO_3)_3$ [AB(RPA)]

AB(RPA) were synthesized by the hydrothermal method. 1 mmol of $ABO_3$ was added to a 0.124 M solution of organophosphonic acid, $RPO_3H_2$, and the reaction mixture was sealed in a Teflon-lined steel bomb. The bomb was heated to 150° C. for 72 h. The powder products were filtered via vacuum filtration and washed with ethanol to remove unreacted reagents. The samples were dried in a convection oven overnight at 80° C.

Melt Synthesis of $AB(RPO_3)_3$ [AB(RPA)]

$AB(RPA)_3$ were synthesized by a melt reaction involving stoichiometric amounts of $ABO_3$ (1 mmol) and 10% molar excess of organophosphonic acid (3.1 mmol). The starting reagents were thoroughly mixed in a mortar and pestle for thirty minutes, before being transferred to sealed glass tubes. The reagents were heated to slightly above the melting point of the organophosphonic acid for 12 hours. The resulting product was then washed with ethanol while under sonication to remove excess organophosphonic acid. After washing with ethanol, the products were centrifuged and the supernatant was removed. The resulting product was then allowed to dry in a convection oven at 80° C. overnight.

PS Film Preparation for Dielectric Measurements

Polystyrene (PS, average MW~100,000) was dissolved in 20 mL of toluene in a glass beaker under rigorous magnetic stirring for 4 hours. Composite materials ($ABO_3$ and AB(RPA)) were added such that the weight percentage of the inorganic material was 40 and stirred for 15 hours to obtain a slurry. The viscosity of the slurry was adjusted by adding toluene. A thin aluminum foil (average thickness 15 µm) was carefully wrapped around a suitable substrate (silicon or pyrex discs), which served as the bottom electrode. Air was blown on the surface for 10 minutes and was cleaned thoroughly with ethanol. Next, the PS-composite slurry was spin-coated on these substrates at 1000 rpm for 15 seconds. The spin-coated substrate was then placed in an oven at 80° C. under vacuum for 12 hours. Finally, parallel plate capacitors were formed by sputter depositing aluminum or gold as top electrodes on the film surface through a shadow mask. The results show no significant variation between Al—Al and Au—Al capacitors.

Results and Discussion

Powder X-Ray Diffraction

Figure 2:
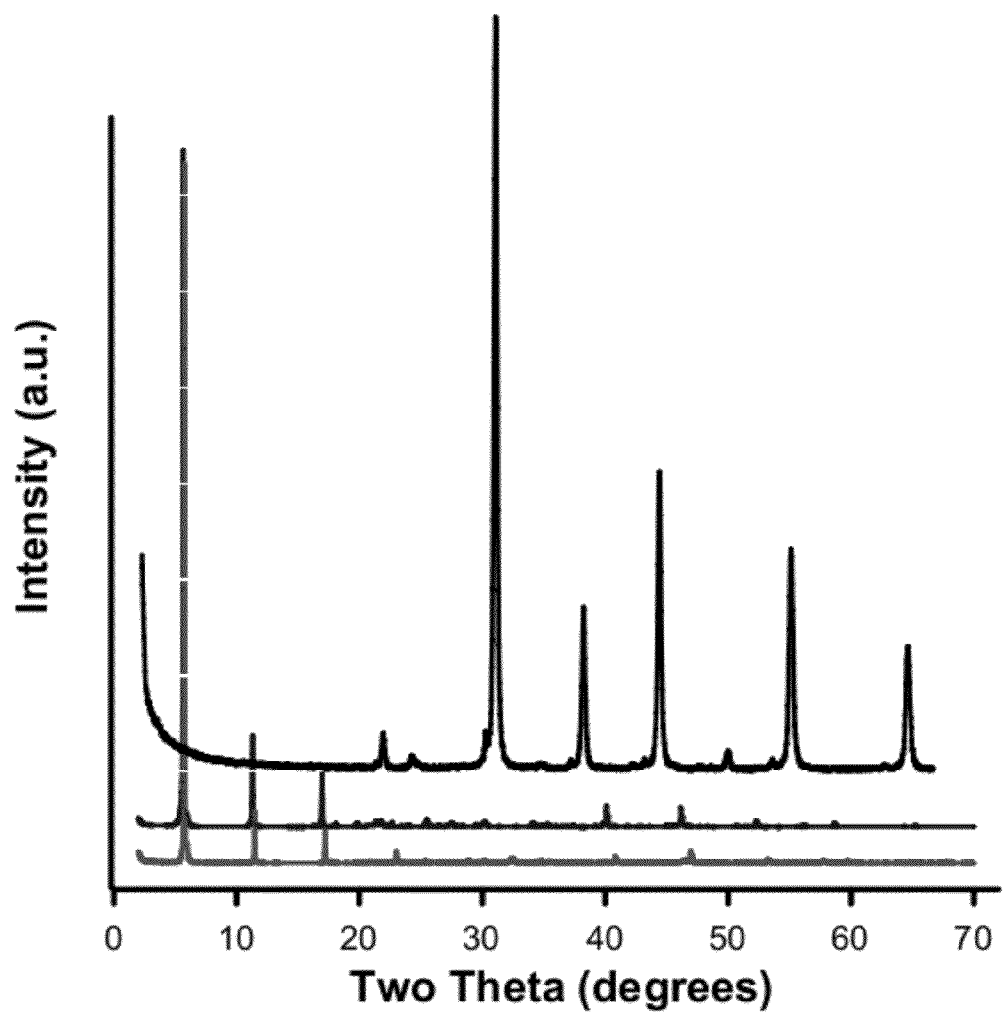
FIG. 2 shows powder XRD patterns of BaTi(PPA)$_3$ (middle pattern), SrTi(PPA)$_3$ (bottom pattern), and SrTiO$_3$ (top pattern) according to the Examples.

Phase purity of the final products, $BaTi(PPA)_3$ and $SrTi(PPA)_3$ were checked by powder X-ray diffraction. FIGS. 1 and 2 show the diffraction patterns of the starting materials and the products. The diffraction patterns of $BaTi(PPA)_3$ and $SrTi(PPA)_3$ consist of several evenly spaced low-angle peaks that are characteristic of 001 reflections of layered solids. The diffraction lines for $BaTi(PPA)_3$ and $SrTi(PPA)_3$ overlay almost perfectly, indicating that both the compounds are structurally similar. This similarity is to be expected given that both compounds contain the same pendant phenyl group. Furthermore, the slight shift of the $BaTi(PPA)_3$ pattern toward lower angles is consistent with the larger size of barium relative to strontium. Attempts to index the powder X-ray diffraction patterns resulted in an interlayer separation of 15.754(1) Å and 15.351(1) for $BaTi(PPA)_3$ and $SrTi(PPA)_3$, respectively. Due to preferred orientation, only the first three diffraction lines could be used to index the patterns. The diffraction pattern for the single metal phosphonate, $Ti(PPA)_2$ (see supporting information), is featureless, indicating an amorphous structure[30]. Data from NMR, TGA, and XRD of thermal degradation products (vide infra) support the assertion that the reaction product is a mixed metal phosphonate, $BaTi(PPA)_3$, rather than a mixture of layered Ba(PPA) and amorphous $Ti(PPA)_2$.

$^{31}P$ MAS NMR Experiments $^{31}P$ MAS NMR experiments were carried out to investigate the phosphorous environments in $BaTi(PPA)_3$, in the physical 1:1 mixture of Ba(PPA) and $Ti(PPA)_2$, and in the solvothermal Ba+Ti+PPA product. $^{31}P$ MAS NMR spectra for the pure metal phosphonates, $Ti(PPA)_2$ and Ba(PPA) were also collected to compare them with the phosphorous environments in the mixed metal samples. The presence of peaks in the $^{31}P$ MAS NMR spectra provides a qualitative indication of different phosphorous environments in the various samples.

Figure 4:
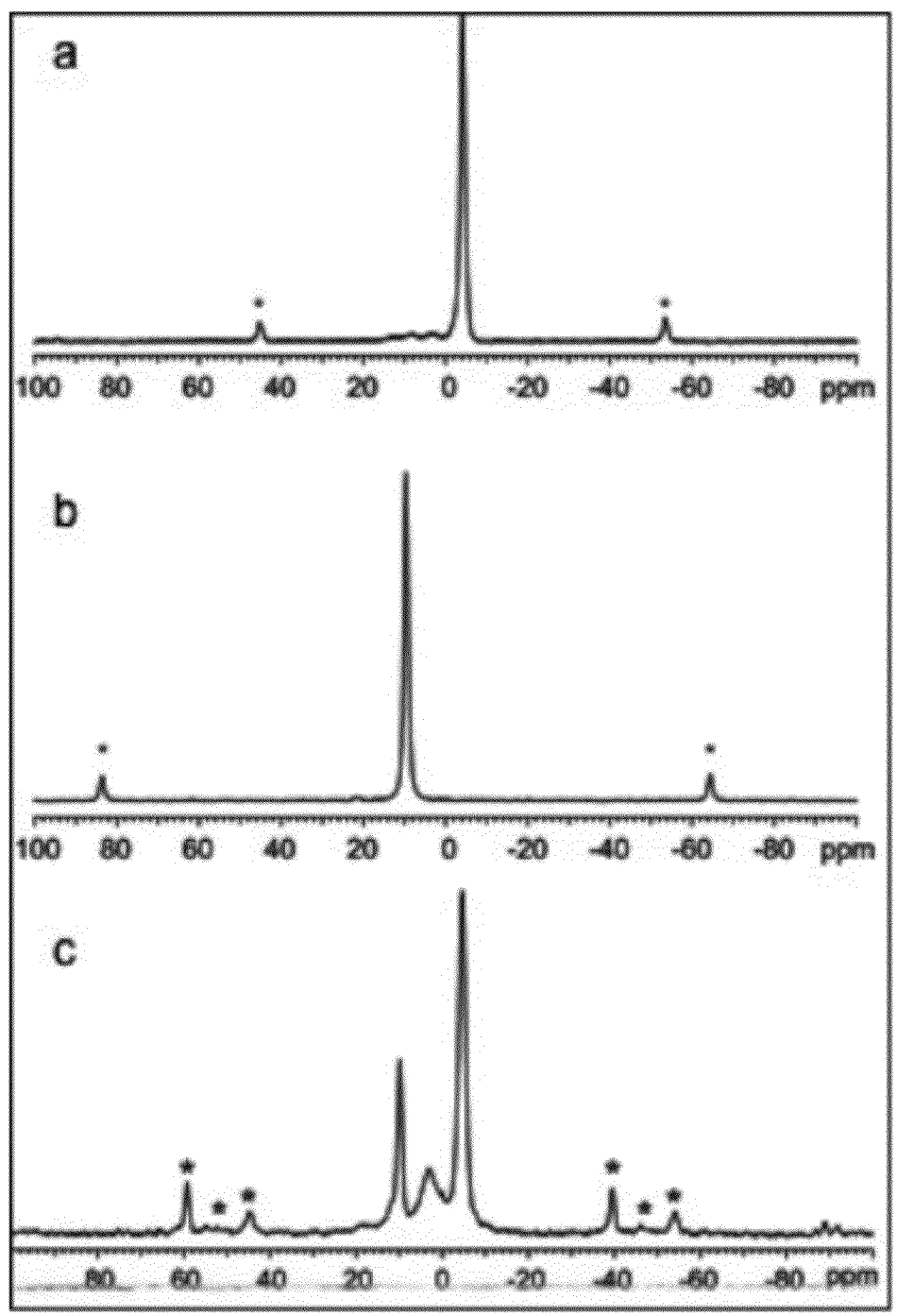
FIG. 4 shows the $^{31}$P MAS NMR spectra of a) Ti(PPA)$_2$, b) Ba(PPA), and c) BaTi(PPA)$_3$ according to the Examples.

The phosphorous environments differ in $Ti(PPA)_2$ vs. Ba(PPA). In the $Ti(PPA)_2$ structure, the octahedral coordination sphere around each $Ti^{+4}$ cation consists of six oxygens from six different phosphonate groups; each phosphonate group bridges three $Ti^{+4}$ cations. A consequence of this structural arrangement is that the $TiO_6$ octahedra are isolated from each other. By comparison, in the Ba(PPA) structure, the coordination environment around each $Ba^{+2}$ cation consists of six oxygens, two of which belong to a single phosphonate group, three of which belong to three other different phosphonate groups, and one that is part of a water molecule; each phosphonate group bridges three $Ba^{-2}$ cations. A consequence of this structural arrangement is that each $BaO_6$ octahedron is connected via a shared oxygen to four other $BaO_6$ octahedra. In both $Ti(PPA)_2$ and Ba(PPA), the crystal structure suggests that the phosphorous will have a single coordination environment in each of these materials. This is confirmed by the $^{31}P$ MAS NMR spectra. The $^{31}P$ resonances in $Ti(PPA)_2$ and Ba(PPA), as shown in FIGS. 4a and 4b, occur at −3.92 ppm and 9.25 ppm respectively, indicating that in each structure there is only a single, unique phosphorous environment. It is important to point out that the chemical shift of 12.40 ppm, observed in the protonated $Ba(C_6H_5PO_3H)_2$, is not seen, and that only the chemical shift of 9.25 ppm, associated with the deprotonated $BaC_6H_5PO_3$, is seen.

In contrast, the $^{31}P$ MAS NMR experiments indicate that in $BaTi(PPA)_3$ (FIG. 4c), three distinct phosphorous environments are present. The first phosphorous peak at −3.95 ppm (s) corresponds to the $M^{4+}$-O—P environment found in $Ti(PPA)_2$ as seen in the standard $^{31}P$ MAS-NMR spectrum of pure $Ti(PPA)_2$. Another phosphorous resonance is observed at 9.25 ppm and corresponds to the $M^{2+}$-O—P environment in Ba—O—P as seen in the standard $^{31}P$ MAS NMR spectrum of pure Ba(PPA). An integration of the area under the peaks indicates that the resonances correspond to ⅓ Ba—O—P to ⅔ Ti—O—P. This is in good agreement with the expected composition and structure of $BaTi(PPA)_3$, where charge balance would dictate that one PPA group is associated with each divalent barium and two PPA groups are associated with each tetravalent titanium. A third phosphorous resonance is observed at 3.38 ppm in the $BaTi(PPA)_3$ material. This is a new resonance and has no counterpart in either of the single metal phosphonates. The third phosphorous environment, located between the other two phosphorous resonances, is unique to the $BaTi(PPA)_3$ structure and suggests a phosphorous environment influenced by both the titanium and the barium. We believe that this environment corresponds to the phosphonate bridging motif Ba—O—P—O—Ti.

Figure 5:
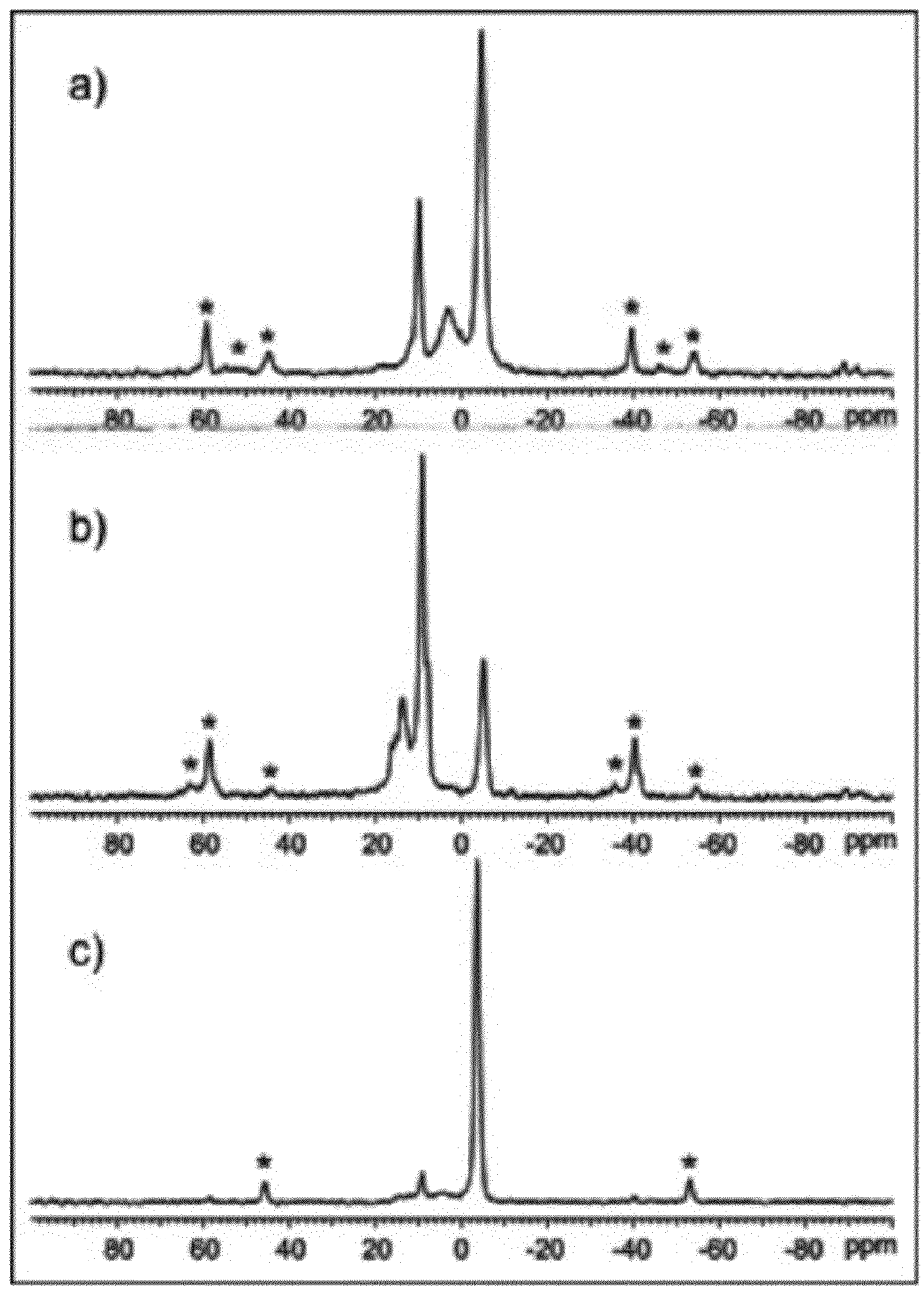
FIG. 5 shows the $^{31}$P MAS NMR spectra of a) BaTi(PPA)$_3$, b) physical mix, and c) solvothermal mix according to the Examples.

Consistent with this assignment of the resonance at 3.38 ppm is the observation that this resonance is not observed in simple physical mixtures of the two individual metal phosphonates. In the $^{31}P$ spectrum for the physical mixture (FIG. 5b), we do not observe the 3.38 ppm resonance, although we do see an additional resonance at 12.40 ppm[33], due to the presence of $Ba(PPAH)_2$, an impurity that forms during the Ba(PPA) synthesis. In the $^{31}P$ spectrum for the solvothermal mixture, FIG. 5c, the 3.38 ppm resonance is again not observed. However the spectrum does show a strong peak associated with the kinetically favored product, $Ti(PPA)_2$ as well as a weak resonance due to the presence of a small amount of Ba(PPA).

Figure 6:
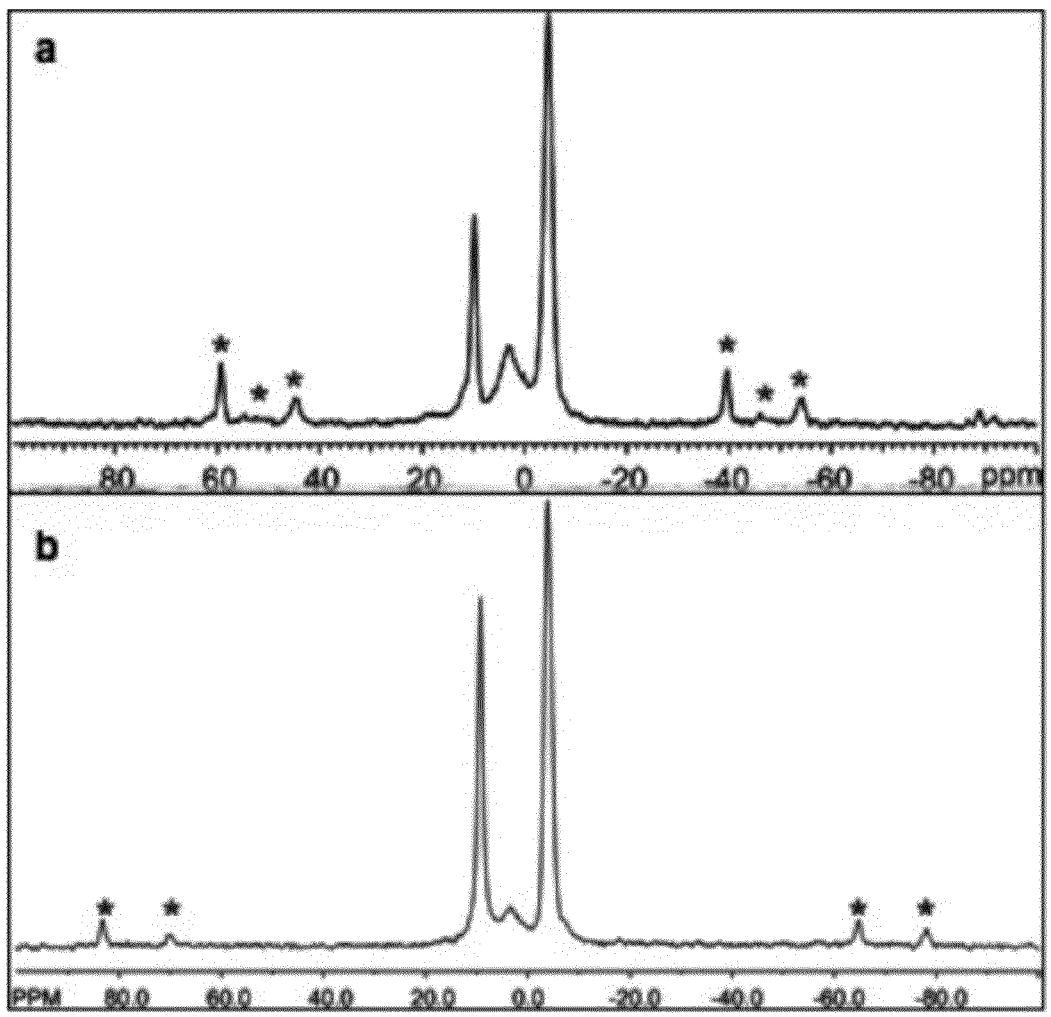
FIG. 6 shows the $^{31}$P MAS NMR spectra of mixed-metal phosphonates a) BaTi(PPA)$_3$ and b) SrTi(PPA)$_3$ according to the Examples.

Analogous results are obtained for $SrTi(PPA)_3$. FIG. 6 compares the $^{31}P$ MAS NMR spectra for $SrTi(PPA)_3$ and $BaTi(PPA)_3$. The $^{31}P$ MAS NMR spectra for $SrTi(PPA)_3$ shows three phosphorous environments like $BaTi(PPA)_3$. The first phosphorous environment located at 10.08 ppm relates to the Sr—O—P and the Ti—O—P environment is located at −4.31 ppm. Similar to the $BaTi(PPA)_3$ material, a third phosphorous environment is seen between the Sr—O—P and Ti—O—P environments at 3.15 ppm. We believe that this phosphorous environment corresponds to the Sr—O—P—O—Ti bridging motif.

Infrared Spectroscopy

FTIR spectra (FIG. 3) provided the insight into the binding of the phenyl phosphonic acid to the mixed metal oxides. Binding is evidenced through the strong C—H phenyl stretching frequency at 3053 cm$^{-1}$. The C=C aromatic stretches are seen at 1590, 1484, and 1436 cm$^{-1}$. Two P—O stretches are seen: M$^{2+}$-O—P at 1213 cm$^{-1}$ and M$^{4+}$-O—P at 1148 cm$^{-1}$. Finally the out-of-plane bending of the mono-substituted phenyl ring is seen at 746, 718, and 685 cm$^{-1}$.

Thermal Analysis.

Figure 7:
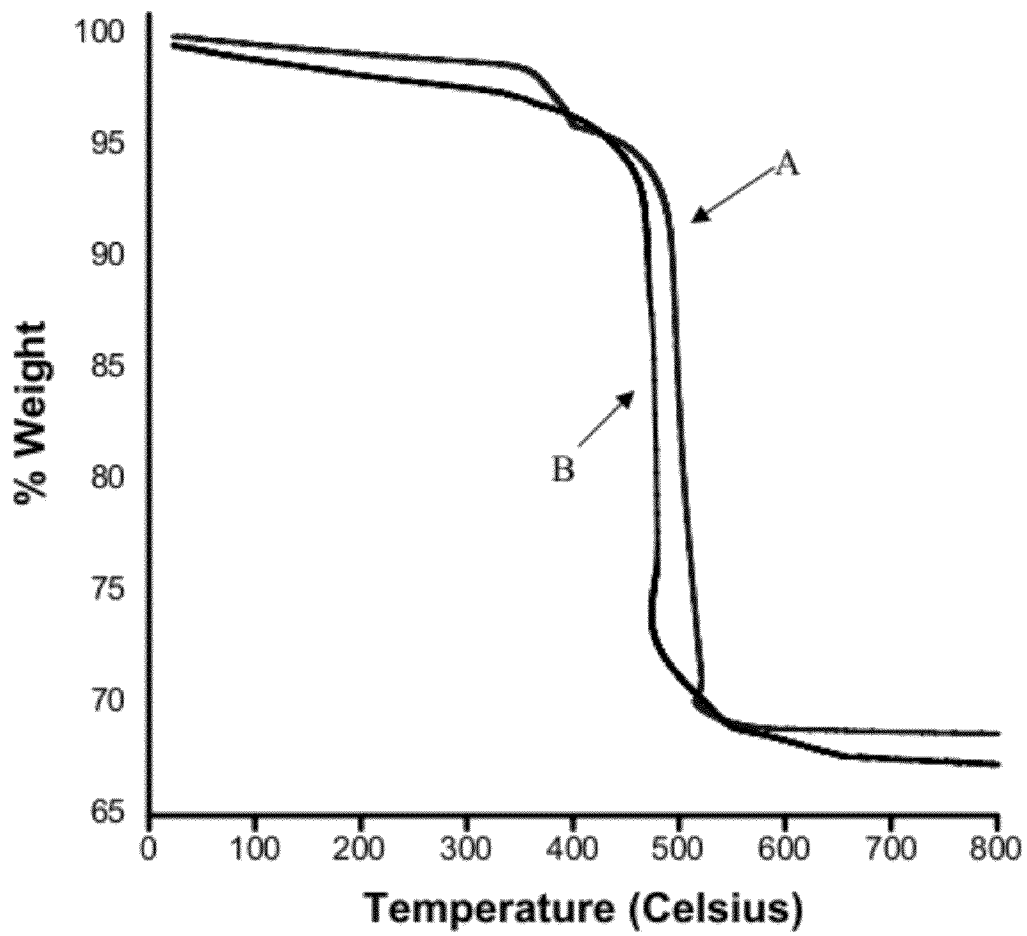
FIG. 7 shows the thermal gravimetric curves of BaTi(PPA)$_3$ (labeled "A") and SrTi(PPA)$_3$ (labeled "B"), according to the Examples.
Figure 8:
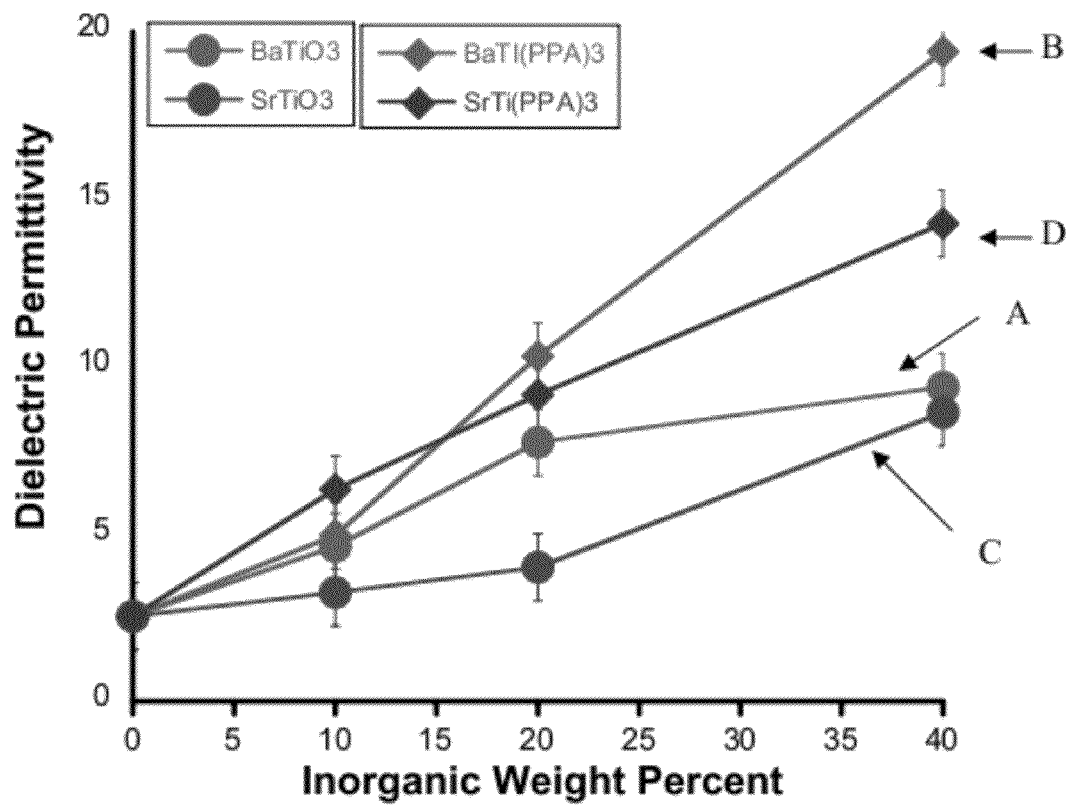
FIG. 8 shows the dielectric constant values of polystyrene composites as a function of weight loading, where A is BaTiO$_3$, B is BaTi(PPA)$_3$, C is SrTiO$_3$, and D is SrTi(PPA)$_3$, according to the Examples.
Figure 12:
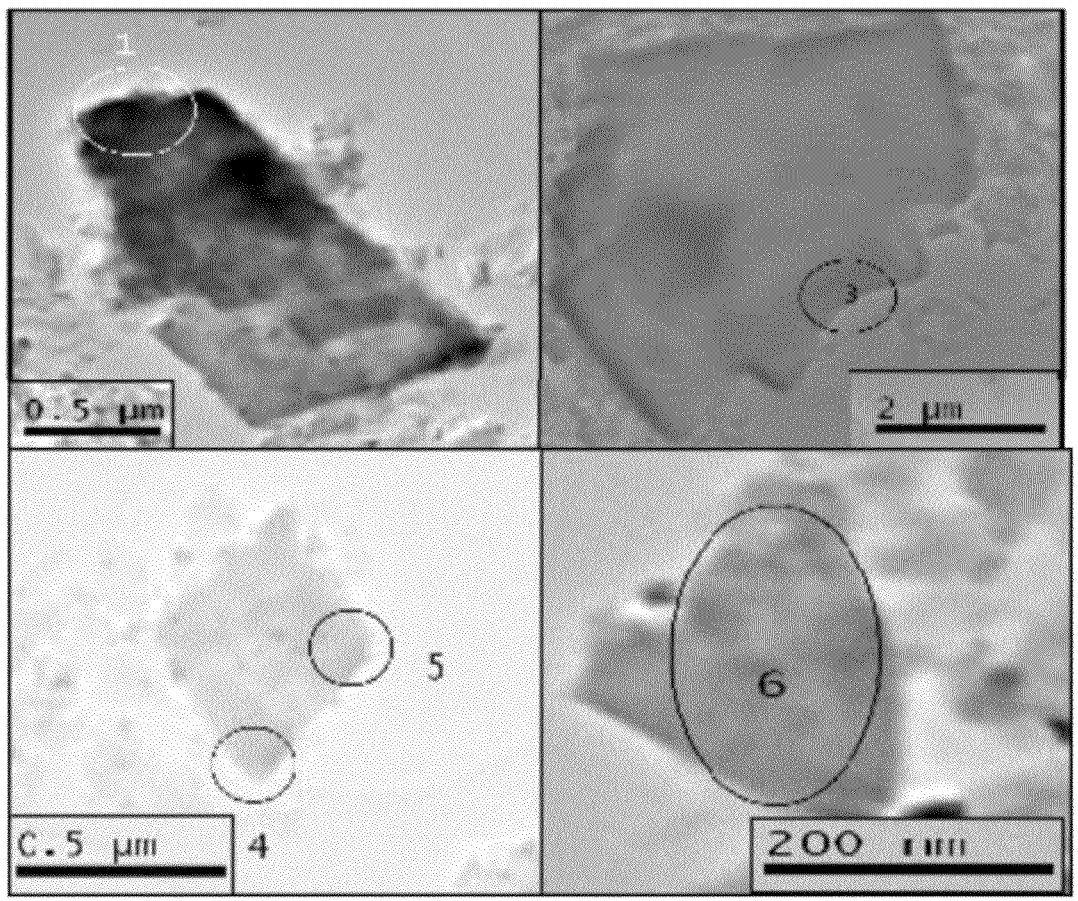
FIG. 12 shows the HRTEM images along with the corresponding sections used for the EDS analysis of a single stack of the mixed-metal phosphonate made according to the Examples.
Figure 13:
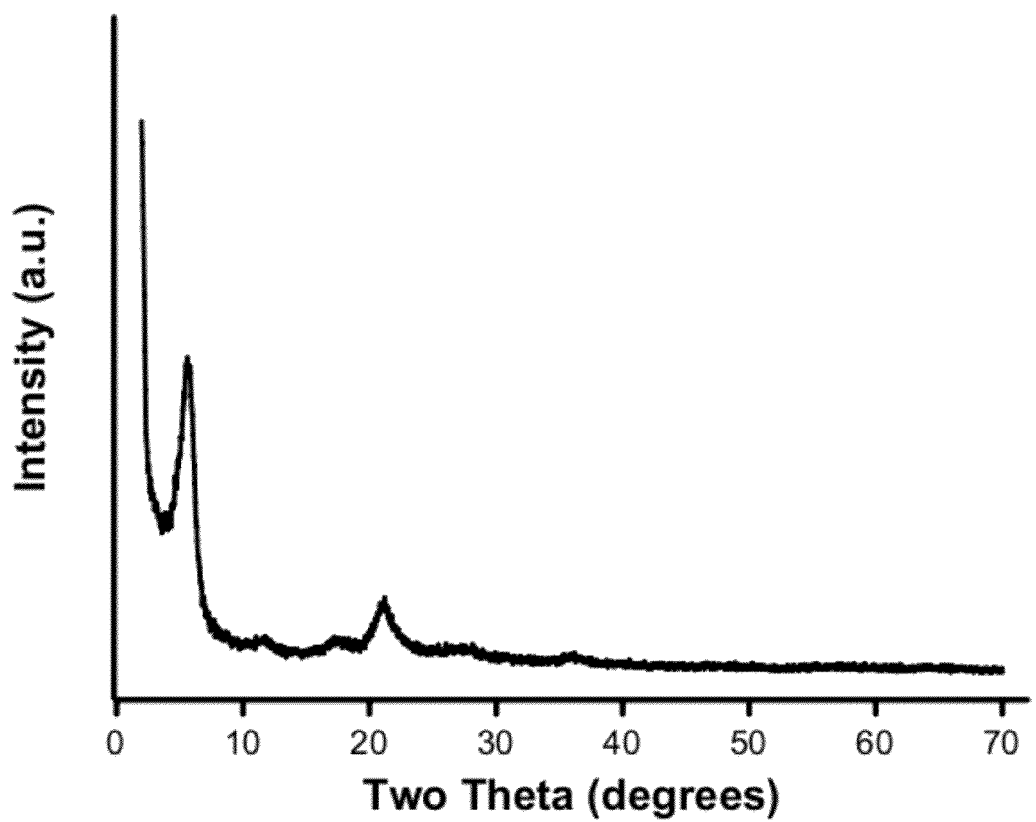
FIG. 13 shows the powder X-ray diffraction data collected on Ti(PPA)$_2$, made according to the Examples.
Figure 14:
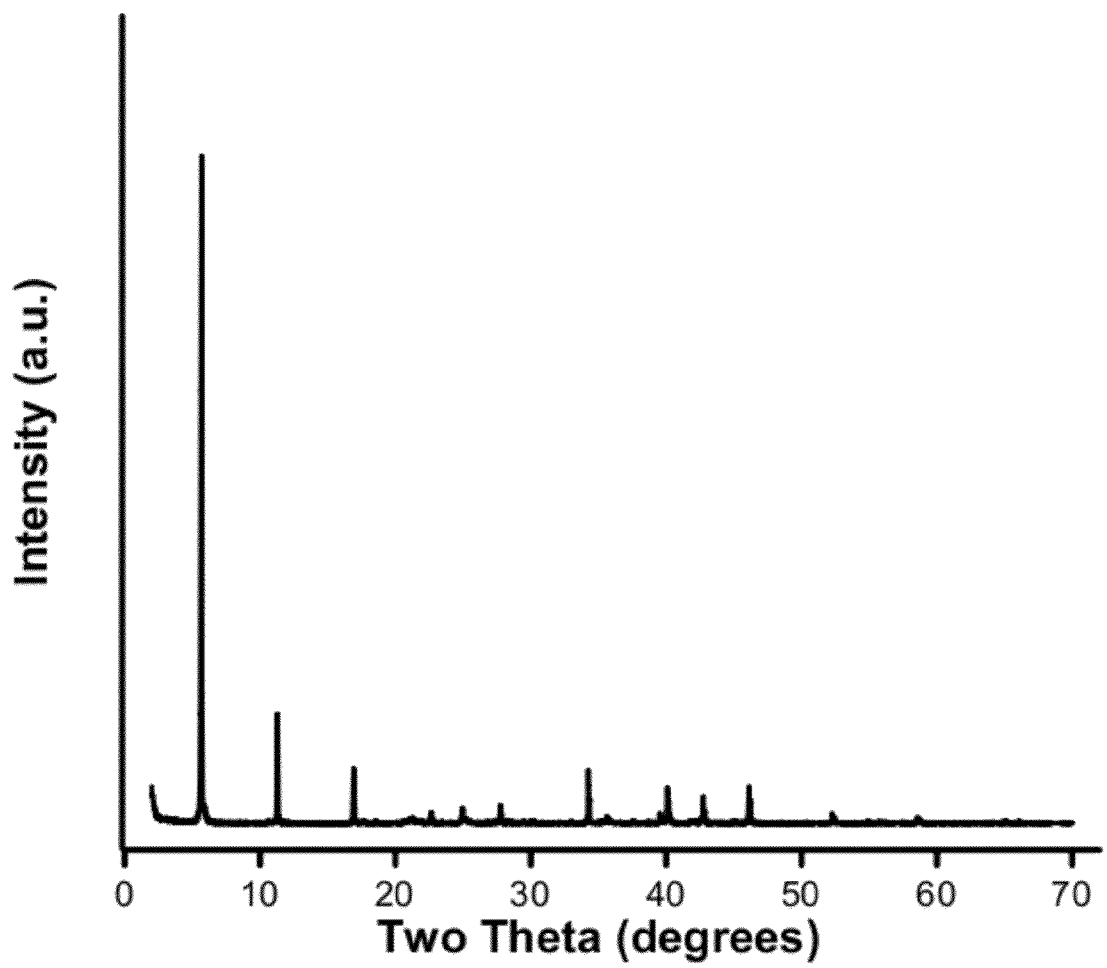
FIG. 14 shows the powder X-ray diffraction data collected on solvothermal mix, made according to the Examples.
Figure 15:
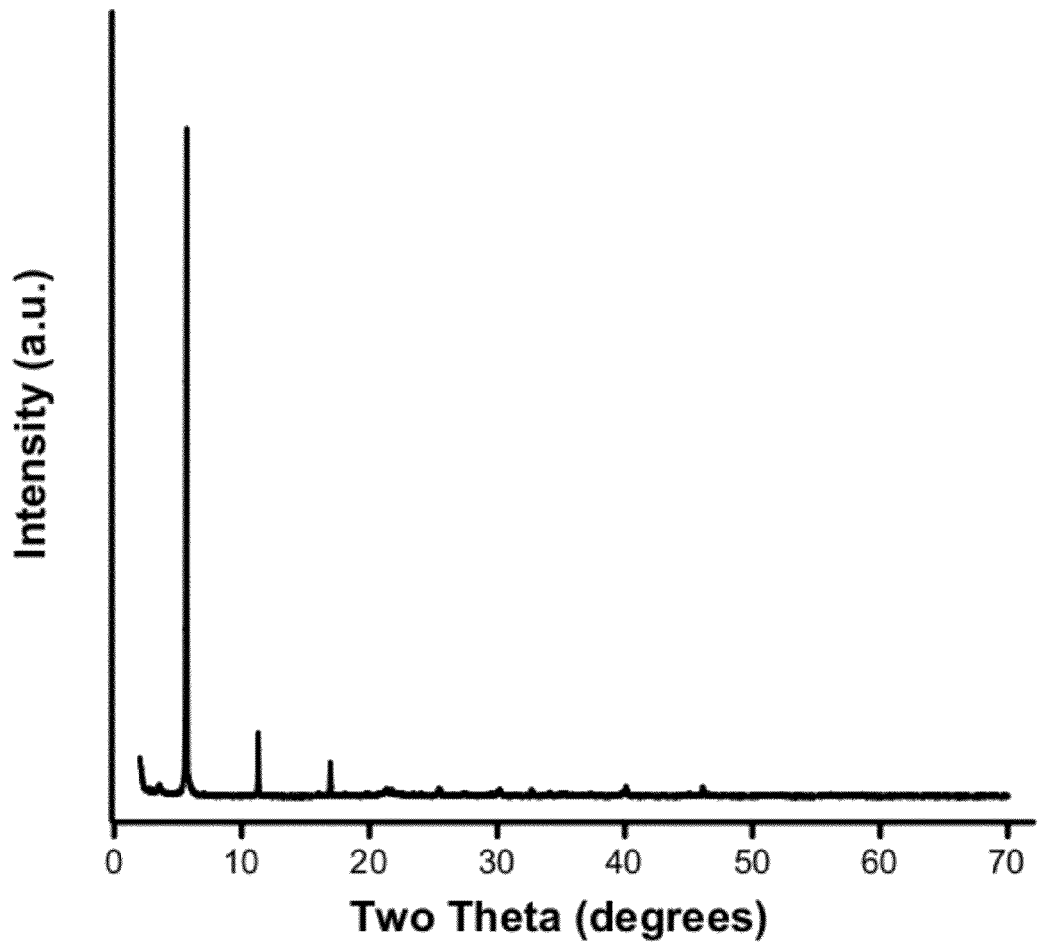
FIG. 15 shows the powder X-ray diffraction pattern of the physical mixture of Ba(PPA) and Ti(PPA)$_2$.

To determine the thermal stability and degradation products of the mixed metal phosphonates, thermal gravimetric experiments coupled with powder XRD were carried out. The thermal degradation process of the mixed metal phenyl phosphonates is seen in FIG. 7. Powder XRD analyses of the thermal degradation products confirm the formation of MTi $(P_2O_7)_{1.5}$. Our observed weight loss corresponds to the loss of three phenyl groups. Both mixed metal phenyl phosphonates show incredible thermal stability near 600° C. as seen in the thermal gravimetric curves of the mixed metal phosphonates seen in FIG. 12.

Platelet Elemental Analysis with XPS and HRTEM/EDS

To analyze the chemical composition of the mixed-metal phosphonates and to confirm the layered structure of these materials high-resolution transmission electron microscopy (HRTEM) images were collected and energy dispersive spectroscopy (EDS) data for the samples were obtained. EDS was used to determine the metal composition of the mixed metal phosphonates. Due to the peak overlap associated with Ba and Ti in EDS, which prevents a quantitative analysis, only SrTi(PPA)$_3$ was studied in detail by HRTEM/EDS.

Figure 3:
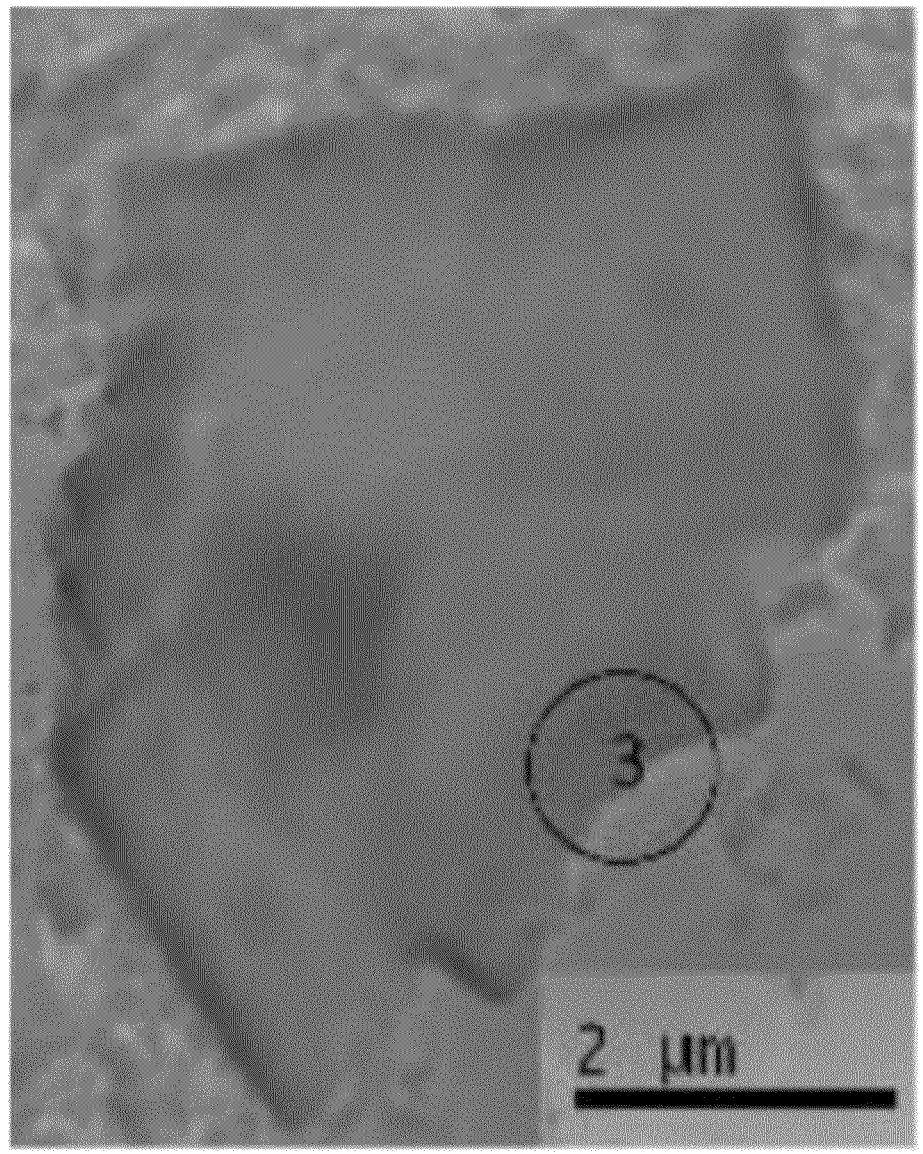
FIG. 3 shows HRTEM imaging of SrTi(PPA)$_3$ according to the Examples. The area circled and labeled 3 represents the EDS spectra taken.

To establish the presence of both strontium and titanium in the same platelet, HRTEM coupled with EDS was carried out on the SrTi(PPA)$_3$ sample dispersed in toluene. FIG. 3 shows an HRTEM image of a single platelet of SrTi(PPA)$_3$. The metal composition of the indicated area on the platelet is 51% Sr and 49% Ti. The EDS data collected on several such platelets, summarized in FIG. 16 (images given in Supporting Information), demonstrate that within experimental error, the ratio of Sr:Ti present in each platelet is 1:1. This is consistent with the result of XPS analysis of the bulk powder (FIG. 16). Overlap of Ba and Ti peaks in EDS prevents quantitative analysis by the this method, however XPS analysis of BaTi (PPA)$_3$ does show a 1:1 ratio of metals.

Dielectric Properties.

Figure 9:
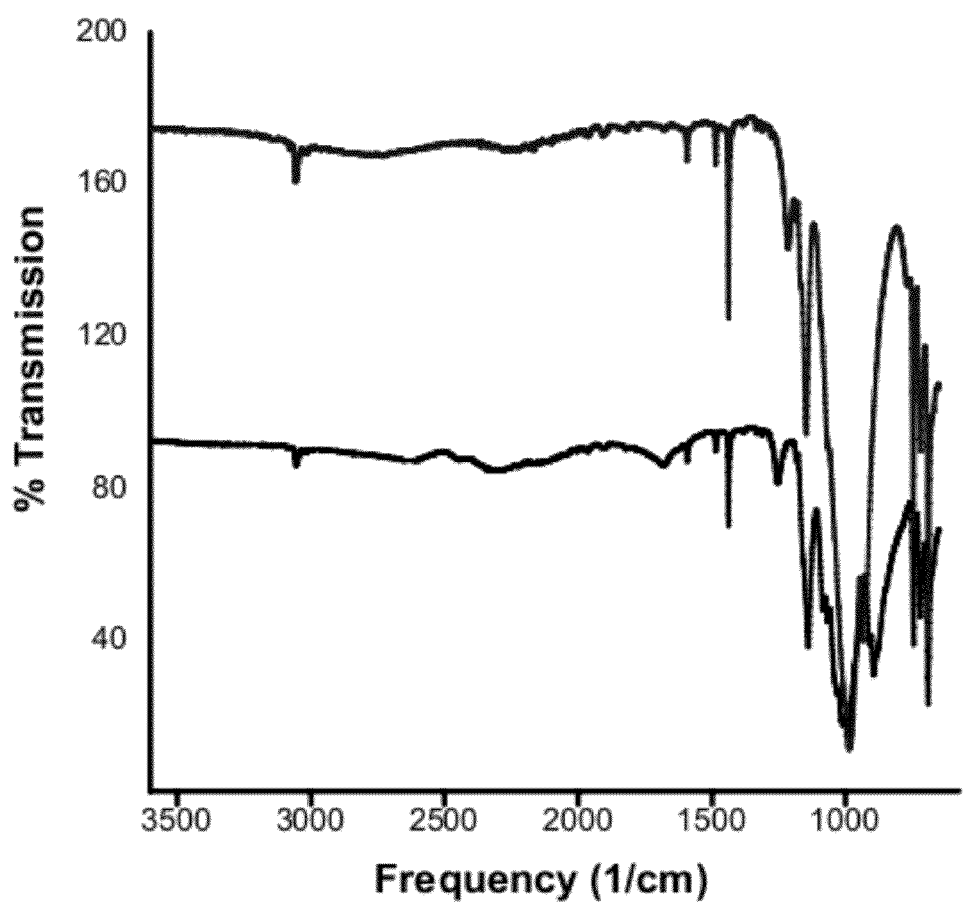
FIG. 9 shows the IR spectra of BaTi(PPA)$_3$ (top plot) and SrTi(PPA)$_3$ (bottom plot).

FIG. 9 shows the dielectric constant as a function of inorganic weight loading for polystyrene (PS) composites incorporating the two titanates (BaTiO$_3$ and SrTiO$_3$) and the two corresponding mixed metal phosphonates [BaTi(PPA)$_3$ and SrTi(PPA)$_3$]. Each data set also includes the value for pure PS, 2.6±0.1, plotted at 0 wt %. For the titanates, the dielectric constants increase by a factor of nearly four as weight loading increases to 40 wt % (to 9.4±0.5 for BaTiO$_3$, and to 8.6±0.2 for SrTiO$_3$). The dielectric constants of the mixed metal phosphonates also increase considerably with inorganic weight loading and are significantly higher than the corresponding titanates at almost every point. At 40 wt %, the dielectric constant of SrTi(PPA)$_3$ is 66% higher (14.3±0.3) than that of SrTiO$_3$. The dielectric constant of BaTi(PPA)$_3$ is 106% higher (19.4±0.2) than that of BaTiO$_3$ and more than six times greater than the value for pure PS.

It is also interesting to compare the dielectric constant of a single metal phosphonate with that of the mixed metal phosphonate. The dielectric constant of 40 wt % Ba(PPA) in PS, 4.6±0.1, is significantly lower than the values for either BaTiO$_3$/PS or BaTi(PPA)$_3$/PS at the same weight loading. This suggests that significant enhancement of the dielectric constant depends on the presence of the two different metals joined by a "linker" atom in the inorganic phase. Comparing the M-O—Ti motif (M=Ba or Sr) in the titanates with the putative M-O—P—O—Ti motif in the phosphonates, the latter apparently leads to a consistently higher increment in the effective dielectric constant of the PS composite.

IR Spectroscopy

Figure 10:
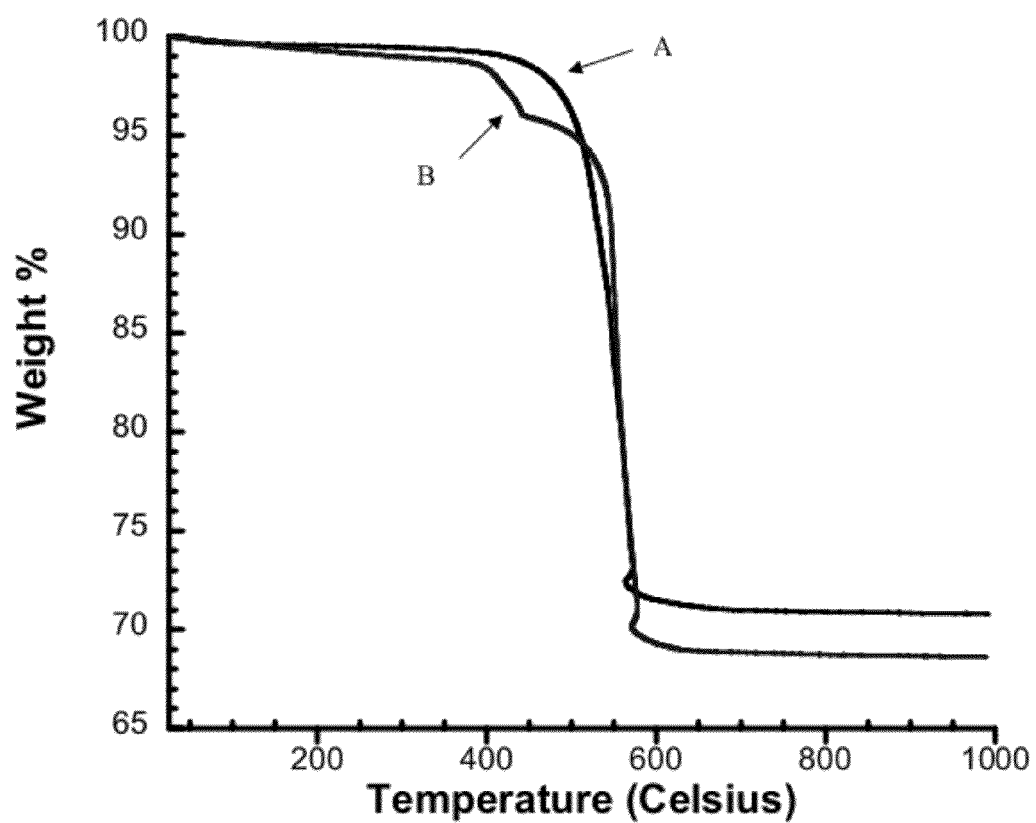
FIG. 10 shows that heating the BaTi(PPA)$_3$ eliminated the coordinated water as evidenced by the TGA curve. BaTi(PPA)$_3$.H$_2$O is labeled "A", while the anhydrous BaTi(PPA)$_3$ is labeled "B".
Figure 11:
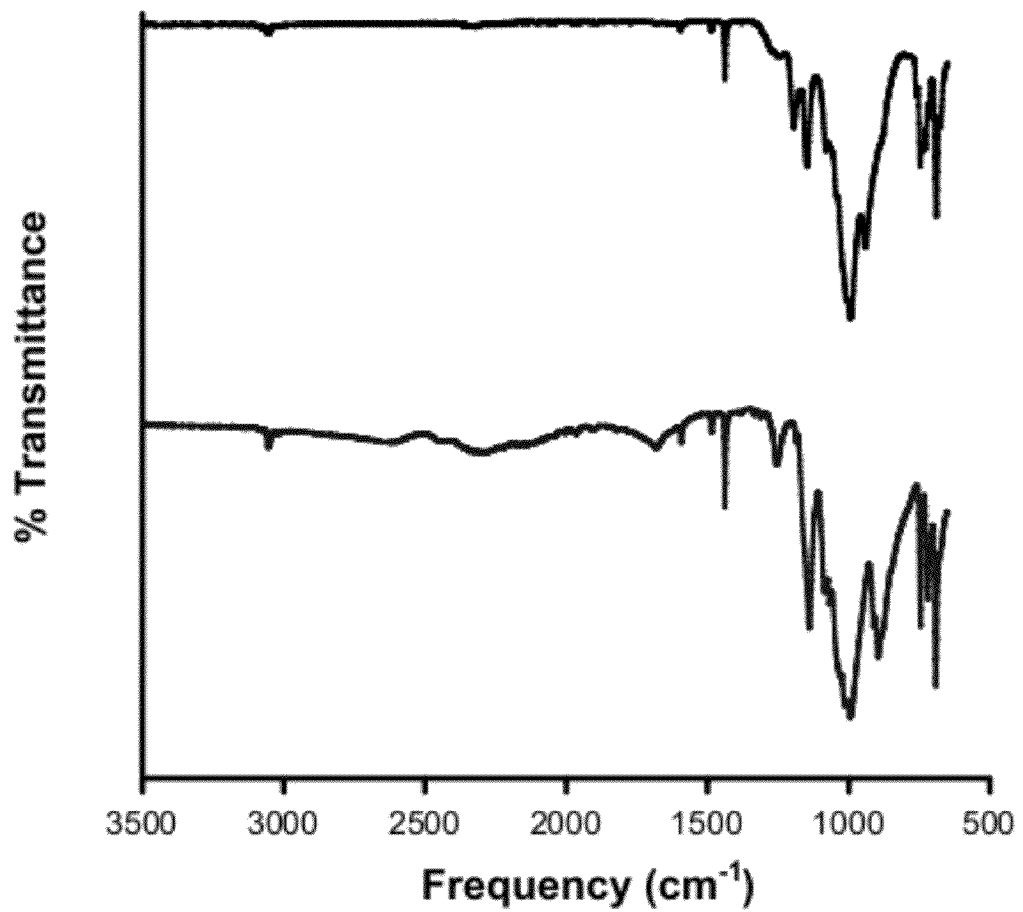
FIG. 11 shows the IR spectra showing loss of coordinated water in the region 2000-2300 cm$^{-1}$, according to the Examples. The top spectrum corresponds to BaTi(PPA)$_3$ heated to 400° C., and the bottom spectrum corresponds to BaTi(PPA)$_3$ with no heating.

FTIR spectroscopy data (FIG. 9) were collected to gain insight into the binding of the phenyl phosphonic acid to the mixed metal oxides. Binding is evidenced through the strong C—H phenyl stretching frequency at 3053 cm$^{-1}$. The C=C aromatic stretches are seen at 1590, 1484, and 1436 cm$^{-1}$. Two P—O stretches are seen: M$^{2+}$-O—P at 1213 cm$^{-1}$ and M$^{4-}$-O—P at 1148 cm$^{-1}$. Finally the out-of-plane bending of the mono-substituted phenyl ring is seen at 746, 718, and 685 cm$^{-1}$. The broad absorptions in the 2000-2300 cm$^{-1}$ region is attributed to the coordinated water on the divalent metal. The coordinated water absorption can be removed by heating sample to 400° C. and is seen in FIG. 10.

Exemplary Mixed Metal Phosphonates ("MMP")

To date, the present inventors have successfully manufactured mixed metal phosphonates of the following formulas, where "PPA" represents phenylphosphonic acid as the precursor to the organophosphonate group:

ATi(PPA)$_3$    (Exemplary MMP 1)

where A is Mg$^{+2}$, Ca$^{+2}$, Sr$^{+2}$, Ba$^{+2}$, Pb$^{+2}$, Co$^{+2}$, Mn$^{+2}$, or Fe$^{+2}$;

AZr(PPA)$_3$    (Exemplary MMP 2)

where A is Ba or Pb;

LaAl(PPA)$_3$; and    (Exemplary MMP 3)

BaTi(RPO$_3$)$_3$    (Exemplary MMP 4)

where R is phenyl, octyl, methyl, and carboxyethyl.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method of making a multi-metal phosphonate, the method comprising combining a multi-metal oxide and an organophosphonic acid in a sealed container; and heating the multi-metal oxide and the organophosphonic acid to a reaction temperature that is above the melting temperature of the organophosphonic acid and below the decomposition temperature of the organophosphonic acid, wherein the multi-metal phosphonate has the composition:

AB(RPO$_3$)$_3$ where

A is Mg$^{2+}$, Ca$^{2+}$, Sr$^{2+}$, Ba$^{2+}$, Pb$^{2+}$, La$^{3+}$, Co$^{2+}$, Mn$^{2+}$, Fe$^{2+}$, or combinations thereof;

B is Ti$^{4+}$, Zr$^{4+}$, Al$^{3+}$, or combinations thereof; and

R is an organic group.

2. The method as in claim 1, further comprising
collecting the multi-metal phosphonate as a precipitate product from the reaction of the multi-metal oxide and the organophosphonic acid.

3. The method as in claim 1, wherein R comprises an aryl group, a phenyl group, an alkyl group, or an alkenyl group.

4. The method as in claim 1, wherein A comprises $Ba^{2+}$.

5. The method as in claim 1, wherein B comprises $Ti^{4+}$.

6. The method as in claim 1, wherein the multi-metal phosphonate has the composition: $BaTi(PPA)_3$, where PPA represents phenylphosphonic acid as the precursor to the organophosphonate group.

7. The method as in claim 1, wherein the multi-metal phosphonate has the composition:

$$ATi(PPA)_3$$

where A is $Mg^{2+}$, $Ca^{2+}$, $Sr^{2+}$, $Ba^{2+}$, $Pb^{2+}$, $Co^{2+}$, $Mn^{2+}$, or $Fe^{2+}$; and where "PPA" represents phenylphosphonic acid as the precursor to the organophosphonate group.

8. The method as in claim 1, wherein the multi-metal phosphonate has the composition:

$$AZr(PPA)_3$$

where A is $Ba^{2+}$ or $Pb^{2+}$; and where "PPA" represents phenylphosphonic acid as the precursor to the organophosphonate group.

9. The method as in claim 1, wherein the multi-metal phosphonate has the composition:

$$LaAl(PPA)_3;$$

where "PPA" represents phenylphosphonic acid as the precursor to the organophosphonate group.

10. The method as in claim 1, wherein the multi-metal phosphonate has the composition:

$$BaTi(RPO_3)_3$$

where R is phenyl, octyl, methyl, and carboxyethyl.

11. The method as in claim 1, further comprising:
forming a polymeric film comprising a polymeric material and the multi-metal phosphonate.

12. The method as in claim 1, wherein the multi-metal oxide comprises $$ABO_3$$

where
A is $Mg^{2+}$, $Ca^{2+}$, $Sr^{2+}$, $Ba^{2+}$, $Pb^{2+}$, $La^{3+}$, $Co^{2+}$, $Mn^{2+}$, $Fe^{2+}$, or combinations thereof; and
B is $Ti^{4+}$, $Zr^{4+}$, $Al^{3+}$, or combinations thereof.

13. The method as in claim 1, wherein the organophosphonic acid comprises $RPO_3H_2$, where R is the organic group.

14. The method as in claim 13, wherein R is a phenyl group.

15. A method of making a multi-metal phosphonate, the method comprising
combining a multi-metal oxide and an organophosphonic acid in a solvent; and
boiling the solvent containing the multi-metal oxide and the organophosphonic acid,
wherein the multi-metal phosphonate has the composition:

$$AB(RPO_3)_3$$

where
A is $Mg^{2+}$, $Ca^{2+}$, $Sr^{2+}$, $Ba^{2+}$, $Pb^{2+}$, $La^{3+}$, $Co^{2+}$, $Mn^{2+}$, $Fe^{2+}$, or combinations thereof;
B is Ti4+, Zr4+, Al3+, or combinations thereof; and
R is an organic group.

16. The method as in claim 15 further comprising
collecting the multi-metal phosphonate as a precipitate.

17. The method as in claim 15, wherein the multi-metal oxide comprises $$ABO_3$$

where
A is $Mg^{2+}$, $Ca^{2+}$, $Sr^{2+}$, $Ba^{2+}$, $Pb^{2+}$, $La^{3+}$, $Co^{2+}$, $Mn^{2+}$, $Fe^{2+}$, or combinations thereof; and
B is $Ti^{4+}$, $Zr^{4+}$, $Al^{3+}$, or combinations thereof.

18. The method as in claim 15, wherein the organophosphonic acid comprises $RPO_3H_2$, where R is the organic group.

19. The method as in claim 15, wherein R is a phenyl group.

* * * * *